(12) United States Patent
Ishihara et al.

(10) Patent No.: US 7,973,193 B2
(45) Date of Patent: Jul. 5, 2011

(54) METHOD FOR PRODUCING ESTER CONDENSED PRODUCT

(75) Inventors: Kazuaki Ishihara, Konan (JP); Hisahi Yamamoto, Chicago, IL (US)

(73) Assignee: Japan Science and Technology Agency, Kawaguchi (JP)

( * ) Notice: Subject to any disclaimer, the term of this patent is extended or adjusted under 35 U.S.C. 154(b) by 100 days.

(21) Appl. No.: 12/393,519

(22) Filed: Feb. 26, 2009

(65) Prior Publication Data

US 2009/0187042 A1 Jul. 23, 2009

Related U.S. Application Data

(62) Division of application No. 10/574,056, filed as application No. PCT/JP2004/014474 on Oct. 1, 2004, now abandoned.

(30) Foreign Application Priority Data

Oct. 2, 2003 (JP) .................................. 2003-345089

(51) Int. Cl.
*C07C 69/76* (2006.01)
(52) U.S. Cl. ........................................ 560/105; 560/103
(58) Field of Classification Search .................. None
See application file for complete search history.

(56) References Cited

U.S. PATENT DOCUMENTS

| | | | |
|---|---|---|---|
| 3,455,998 A | 7/1969 | Arpe | 560/242 |
| 4,557,824 A | 12/1985 | Kukes et al. | 208/251 |
| 7,301,045 B2 * | 11/2007 | Ishihara et al. | 560/1 |
| 2002/0045545 A1 | 4/2002 | Oki | 502/350 |
| 2002/0147275 A1 | 10/2002 | Bublewitz | 525/100 |
| 2002/0156186 A1 | 10/2002 | Bublewitz | 525/100 |

FOREIGN PATENT DOCUMENTS

EP  1 334 960 A1  8/2003
(Continued)

OTHER PUBLICATIONS

Fraga-Dubreuil et al., Catalysts Communications, 3 (2002) 185-190.*

(Continued)

*Primary Examiner* — Karl J Puttlitz
(74) *Attorney, Agent, or Firm* — Locke Lord Bissell & Liddell LLP (57) ABSTRACT

The present invention is to provide a method for preparing an ester condensate and a catalyst therefore; wherein the method enables synthesis of enormous amounts of ester condensates comprising a specific structure in good yield, by a reaction of carboxylic acid and alcohol in equimolar amounts, while generation of by-products is prevented; wherein the catalyst exhibits good catalytic efficiency as a catalyst for use, the use of the catalyst in small amount is sufficient, and the catalyst is reusable and can be used repeatedly; therefore, the method for preparing an ester condensate of the present invention and the catalyst therefore can be applied to industrial methods which are preferable in view of green chemistry. Esterification reaction is performed by using a catalyst comprising a zirconium (IV) compound and/or a hafnium(IV) compound and an iron compound and a gallium compound. It is preferable that the zirconium(IV) compound is a compound represented by $Zr(OH)_a(OR^1)_b$, wherein, $R^1$ represents an acyl group or an alkyl group, and each of a and b is 0 or any one of integers of 1 to 4 and the relationship of $a+b=4$ is satisfied, and a zirconium(IV) halide.

13 Claims, 1 Drawing Sheet

FOREIGN PATENT DOCUMENTS

| | | |
|---|---|---|
| JP | 07-291898 | 11/1995 |
| JP | 2002-121170 | 4/2002 |
| JP | 2003-040838 | 2/2003 |

OTHER PUBLICATIONS

Ishihara et al., Science (Washington, D. C.) (2000), 290(5494), 1140-1142.*

Database Caplus Chemical Abstracts Service, Columbus, Ohio, US; Database Accession No. 2002:843987, Abstract of Chu Il et al.: CN 1323655.*

Ishihara, et al., "Direct Ester Condensation From a 1:1 Mixture of Carboxylic Acids and Alcohols Catalyzed by Hafnium (IV) or Zirconium (IV) Salts", 2002, Tetrahedron, 58: 8179-8188.

Nakayama, et al., "Water-Tolerant and Reusable Catalysts for Direct Ester Condensation Between Equimolar Amounts of Carboxylic Acids and Alcohols", 2004, Adv. Synth. Catol., 346: 1275-1279.

Ishihara, et al., "A Green Method for the Selective Esterification of Primary Alcohols in the Presence of Secondary Alcohols or Aromatic Alcohols", 2001, Synlett, No. 7: 1117-1120.

Communication with Supplementary European Search Report for Application No. EP 04 79 1941.

Atsushi Sato et al, "Recovery and Reuse of Zirconium (IV)-Iron(III) Complexes as Highly Active Hybrid Catalysts for Direct Esterification," (*Nagoya Univ., Univ. of Chicago, SORST, JST*) Sato, Atsushi; Ishihara, Kazuski; Yamamoto, Hisashi, Mar. 11, 2004.

Communication from European Patent Office issued in corresponding EP Application No. 04 791 941.0 (dated Aug. 12, 2010).

* cited by examiner

FIG. 1

METHOD FOR PRODUCING ESTER CONDENSED PRODUCT

This application is a divisional application of U.S. patent application Ser. No. 10/574,056 filed Mar. 29, 2006, which is a National Stage entry of the PCT application No. PCT/JP2004/014474 filed Oct. 1, 2004 which claims the priority benefit of Japanese Patent Application Serial No. JP2003-345089 filed Oct. 2, 2003, the contents of each of which are incorporated in their entireties.

TECHNICAL FIELD

The present invention relates to a method for preparing an ester condensate and a catalyst used therefore. More specifically, the present invention relates to a method for preparing an ester condensate and a catalyst used therefore, wherein the method allows preparation of the ester condensate in good yield from equimolar amounts of materials and allows reuse of the recovered catalysts repeatedly, as well as it cuts waste of resources significantly, provides effective use of resources, and reduces environmental destruction.

BACKGROUND ART

Esterification reaction, which is the most basic reaction of organic synthesis, is an important reaction having a great utility value also from the view point of an environmentally-friendly chemical process. An enormous amount of reports have already been made concerning the esterification reaction, but there were problems as follows in view of green chemistry and atom efficiency: one equivalent weight or more of condensing reagent or activator was used for a substrate in many cases; a large quantity of by-products was generated through the reaction, thereby complicated operations for separation and purification become necessary after the reaction; unless either of carboxylic acid or alcohol was used excessively, it was impossible to prepare ester efficiently in many cases (see, e.g., Japanese Laid-Open Patent Application No. 52-75684; *Synthesis.* 1978, p. 929; *Chem. Lett.* p. 55, 1977; *Chem. Lett.* p. 663, 1981; *Tetrahedron. Lett.* 28, p. 3713, 1987; and *J. Org. Chem.* 56, p. 5307, 1991). Excessive use of substrates should actually be avoided, so it would be an ideal process if a direct esterification could be performed from equimolar amounts of carboxylic acid and alcohol. A polyester polymerized catalyst comprising a structure of Ar—O— (Ar represents an aryl group) and the like and one or more of metal compounds selected from the group of scandium, yttrium, zirconium, hafnium, and vanadium, and (see, e.g., Japanese Laid-Open Patent Application No. 2000-154241) is known as a polycondensation catalyst. Additionally, as a method for preparing ester wherein ester can be synthesized in good yield even when approximately equimolar amounts of the raw materials, i.e. acids and alcohols, are used, a method for preparing ester from carboxylic acids and alcohols using an esterification catalyst containing a titanium metal compound selected from the group of halides, nitrate salts, carboxylate salts, alcoholates and acetylacetone-type complex of titanium metal, as at least one of the active ingredients (see, e.g. Japanese Laid-Open Patent Application No. 8-71429) is also known.

Other than those above, followings are known: an ester polycondensation catalyst comprising an aluminum compound and a metal compound other than aluminum (see, e.g., Japanese Laid-Open Patent Application No. 2000-302854), a method for preparing an aliphatic polyester, wherein a germanium compound and at least one of the metal compounds selected from the group of titanium, antimony, zirconium, iron and the like, are used as a catalyst (see, e.g., Japanese Laid-Open Patent Application No. 8-27262), a catalyst for preparing polyester, wherein a compound comprising at least one of the elements selected from the group of beryllium, magnesium, calcium, hafnium, iron and the like and a hydrolysate of a titanium halide (see, e.g., Japanese Laid-Open Patent Applications Nos. 2001-48973 and 2001-64377), and a transesterification catalyst, wherein phosphate ion is contained in one or more of metal oxide and/or metal hydroxide selected from the group of aluminum, zirconium and iron (see, e.g., Japanese Laid Open-Patent Application No. 2001-17862).

However, there was no catalyst as the one used in the above-mentioned esterification reaction with the following features: selective synthesis of ester can be realized in good yield even by using approximately equimolar amounts of carboxylic acid and alcohol as the raw materials; the reaction speed was high at low temperature even when a small amount of catalyst are used; a very small side reaction was occurred; and the catalyst which was reusable by simple processing was used repeatedly, thereby the usage of the catalyst could be significantly reduced.

Since the demand for compounds having complicated structures is increasing for the synthesis of pharmaceuticals, the object of the present invention is to provide a method for preparing an ester condensate and a catalyst therefore; wherein the method enables to synthesize enormous amounts of ester condensates comprising a specific structure in good yield, by a reaction of carboxylic acids and alcohols in equimolar amounts, while generation of by-products is prevented in the synthesis of organic compounds such as the pharmaceuticals; and wherein the catalyst exhibits a good catalytic efficiency as a catalyst for use, the use of the catalyst in small amount is sufficient, and the catalyst being reusable can be used repeatedly; therefore, the method for preparing an ester condensate can be applied to industrial methods which are preferable also in view of green chemistry.

The present inventors have already developed a dehydration-condensation reaction from an-equimolar mixture of carboxylic acid and alcohol, wherein zirconium(IV) salt or hafnium(IV) salt was used for the catalyst. Having promoted the study on esterification reaction, the present inventors performed a condensation reaction as follows: $Zr(OH)_x(OAc)_y$, (x+y=4) as a catalyst was added to a heptane solution of an-equimolar mixture of 4-phenylbutyric acid and cyclododecanol, further 2 mol % of various metal salts as additives were added thereto, the mixture was heated to reflux (the bath temperature: 120° C., 6 hours), and the resultant was brought to azeotropic dehydration. As a result, it was revealed that the catalytic activity is improved by adding metal salts such as $Ga(Oi-Pr)_3$, $Fe(Oi-Pr)_3$, $Al(Oi-Pr)_3$, $Sn(Oi-Pr)_4$ and the like as additives. Among those metal salts, using $Ga(Oi-Pr)_3$ and $Fe(Oi-Pr)_3$ brought particularly good results. Single use of 3 mol % of these additives for performing the reaction in stead of Zr(IV) salt could not induce excellent activity. Although $Ti(Oi-Pr)_4$ is also known as a catalyst having high activity as well as Zr(IV) or Hf(IV) salts, synergistic improvement of the catalytic activity could not be observed by using the combinations of Ti(IV)-Zr(IV), Zr(IV)-Hf(IV), and Ti(IV)-Hf(IV). When the reaction was performed similarly by using Hf(IV) salt, a similar effect to the additive effect on Zr(IV) salt could be obtained.

Next, the relationship between content rate to 10 mol % of $Zr(Oi-Pr)_4$ and the catalytic activity was investigated on $Fe(Oi-Pr)_3$ which showed the most significant additive effect. As the result, it was shown that adding $Fe(Oi-Pr)_3$ into $Zr(Oi-$ Pr)₄ little by little improved the catalytic activity which kept enhancing until the content rate of Fe(Oi-Pr)₃ reached to 0.5 mol %; even if the rate of Fe(Oi-Pr)₃ was further increased, the catalytic activity showed little change. Accordingly, it is substantially appropriate that the molar ratio of Zr(Oi-Pr)₄ to Fe(Oi-Pr)₃ is between 20 to 1 and 1 to 1.

Next, the change with time was studied on ester condensation reaction using composite metal salt catalysts, Zr(Oi-Pr)₄—Fe(Oi-Pr)₃, Hf(Oi-Pr)₄—Fe(Oi-Pr)₃, and Ti(Oi-Pr)₄—Fe(Oi-Pr)₃. As the result, it was revealed that Zr(IV)-Fe(III) had approximately equal level of catalytic activity to that of Hf(IV)-Fe(III); a significant accelerating effect of the reaction could not be observed with Ti(IV)-Fe(III).

Further, as the result of consideration of reusability of catalysts in order to promote green chemistry, it was demonstrated that solids had an equivalent catalytic effect to that of Zr(Oi-Pr)₄—Fe(Oi-Pr)₃, which was resulted by adding 1 M hydrochloric acid solution to the mixture of Zr(Oi-Pr)₄ or Hf(Oi-Pr)₄ and Fe(Oi-Pr)₃, stirring the admixture for 0.5 hour at room temperature, and then exsiccating it. Consequently, ester condensation reaction was carried out with 3 mol % of Zr(Oi-Pr)₄ and 4 mol % of Fe(Oi-Pr)₄, then 1 M hydrochloric acid solution was added thereto and ester was obtained from the organic layer by extraction. On the other hand, metal salt was recovered from the aqueous layer, carboxylic acid, alcohol and a reaction solvent were added to the aqueous solution again without concentration, and azeotropic dehydration was carried out by heating to reflux. It was followed by ester condensation reaction proceeding as in the case of the first reaction. The present inventors obtained knowledge that the catalyst can be recovered and reused by repeating this series of operations.

In addition, from the result of considering reusability of a catalyst without using hydrochloric acid, esterification reaction was carried out under heating to reflux with the use of the mixture of Zr(Oi-Pr)₄ or Hf(Oi-Pr)₄ and Fe(Oi-Pr)₃ as a catalyst with azeotropic dehydration in a mixed solvent of a low-polar organic solvent and an ionic liquid. After the reaction was finished, the solution was left at room temperature for sometime, and then it was found that the solution was separated into two layers of an organic solvent layer and an ionic liquid layer. Ester was obtained from the organic layer in the upper part in good yield. On the other hand, carboxylic acid, alcohol and a reaction solvent were added to the solution again without concentrating the ionic liquid layer containing metal salts, and azeotropic dehydration was carried out by heating to reflux. It was followed by ester condensation reaction proceeding as in the case of the first reaction. The present inventors obtained knowledge that the catalyst can be recovered and reused by repeating this series of operations, which led the present inventors to complete the present invention.

DISCLOSURE OF THE INVENTION

The present invention relates to: [1] a method for preparing an ester condensate, wherein an esterification reaction is carried out using a catalyst containing a zirconium (IV) compound and/or a hafnium(IV) compound and an iron(III) compound and/or a gallium(III) compound; [2] the method for preparing an ester condensate according to [1], wherein the zirconium (IV) compound is a compound represented by a general formula (1):

wherein, R¹ represents an acyl group or an alkyl group, and each of a and b is 0 or any one of integers of 1 to 4 and the relationship of a+b=4 is satisfied; [3] the method for preparing an ester condensate according to [1], wherein the zirconium (IV) compound is a compound represented by a general formula (3):

wherein X represents a halogen atom, Y represents tetrahydrofuran, and e represents 0 or 2; [4] the method for preparing an ester condensate according to [1], wherein the hafnium (IV) compound is a compound represented by a general formula (2):

wherein, R² represents an acyl group or an alkyl group, and each of c and d is 0 or any one of integers of 1 to 4 and the relationship of c+d=4 is satisfied; [5] the method for preparing an ester condensate according to [1], wherein the hafnium (IV) compound is a compound represented by a general formula (4):

wherein X represents a halogen atom, Y represents tetrahydrofuran, and f represents 0 or 2; [6] the method for preparing an ester condensate according to any one of [1] to [5], wherein the iron compound is iron(III) alkoxide, and the gallium compound is gallium(III) alkoxide; [7] the method for preparing an ester condensate according to any one of [1] to [6], wherein the abundance of the iron compound is 5 mol % or more in relation to the zirconium (IV) compound and/or the hafnium (IV) compound; [8] the method for preparing an ester condensate according to any one of [1] to [7], wherein the esterification reaction is carried out by heating to reflux with a solvent, and removing azeotropic water from a reaction system; [9] the method for preparing an ester condensate according to [8], wherein a nonpolar or a low-polar solvent is used as the solvent; [10] the method for preparing an ester condensate according to [9], wherein the nonpolar or the low-polar solvent is one or more of solvents selected from the group of toluene, xylene, mesitylene, or anisole; [11] the method for preparing an ester condensate according to any one of [1] to [10], wherein an ionic liquid is added to the reaction system after the esterification reaction is finished, ester is obtained from an organic layer, and then an ionic liquid layer per se is used as a catalytic solution; [12] the method for preparing an ester condensate according to [11], wherein the ionic liquid is 1-butyl-3-methyl imidazolium trifluoromethanesulfonimide, 1-ethyl-3-methylimidazolium trifluoromethanesulfonate; [13] the method for preparing an ester condensate according to [11], wherein the ionic liquid is N-alkylpyridinium trifluoromethane sulfonate imide; [14] the method for preparing an ester condensate according to any one of [1] to [10], wherein a hydrochloric acid aqueous solution is added to the reaction system after the esterification reaction is finished, ester is obtained from an organic layer, and then an aqueous layer per se is used as a catalytic solution; and [15] the method for preparing an ester condensate according to any one of [11] to [14], wherein the low-polar organic solvent such as toluene and heptane is used as the solvent.

The present invention further relates to: [16] the method for preparing an ester condensate according to any one of [1] to [15], wherein the esterification reaction is a reaction of carboxylic acid and alcohol; [17] a catalyst for preparing an ester condensate, which is used in esterification reaction and which contains a zirconium (IV) compound and/or a hafnium (IV) compound, and an iron compound and/or a gallium compound; [18] the catalyst for preparing an ester condensate according to [17], wherein the zirconium (IV) compound is a compound represented by a general formula (1):

$$Zr(OH)_a(OR^1)_b \qquad (1),$$

wherein, $R^1$ represents an acyl group or an alkyl group, and each of a and b is 0 or any one of integers of 1 to 4 and the relationship of a+b=4 is satisfied; [19] the catalyst for preparing an ester condensate according to [17], wherein the zirconium (IV) compound is a compound represented by a general formula (3):

$$ZrX_4Y_e \qquad (3),$$

wherein X represents a halogen atom, Y represents tetrahydrofuran, and e represents 0 or 2; and [20] the catalyst for preparing an ester condensate according to [17], wherein the hafnium (IV) compound is a compound represented by a general formula (2):

$$Hf(OH)_c(OR^2)_d \qquad (2),$$

wherein, $R^2$ represents an acyl group or an alkyl group, and each of c and d is 0 or any one of integers of 1 to 4 and the relationship of c+d=4 is satisfied.

The present invention still further relates to: [21] the catalyst for preparing an ester condensate according to [17], wherein the hafnium (IV) compound is a compound represented by a general formula (4):

$$HfX_4Y_f \qquad (4),$$

wherein X represents a halogen atom, Y represents tetrahydrofuran, and f represents 0 or 2); [22] the catalyst for preparing an ester condensate according to any one of [17] to [21], wherein the iron compound is iron(III) alkoxide, and the gallium compound is gallium(III) alkoxide; [23] the catalyst for preparing an ester condensate according to any one of [17] to [22], wherein the abundance of the iron compound is 5 mol % or more in relation to the zirconium (IV) compound and/or the hafnium (IV) compound; [24] the catalyst for preparing an ester condensate according to any one of [17] to [23], wherein an ionic liquid is added to the reaction system after the esterification reaction is finished, ester is obtained from an organic layer, and then an ionic liquid layer per se is used; [25] the catalyst for preparing an ester condensate according to [24], wherein the ionic liquid is 1-butyl-3-methyl imidazolium trifluoromethanesulfonimide, 1-ethyl-3-methylimidazolium trifluoromethanesulfonate; [26] the catalyst for preparing an ester condensate according to [24], wherein the ionic liquid is N-alkylpyridinium trifluoromethane sulfonate imide; [27] the catalyst for preparing an ester condensate according to any one of [17] to [23], wherein hydrochloric acid aqueous solution is added to the reaction system after the esterification reaction is finished, ester is obtained from an organic layer, and then an aqueous layer per se is used as a catalytic solution; and [28] the catalyst for preparing an ester condensate according to any one of [17] to [27], wherein the esterification reaction is a reaction of carboxylic acid and alcohol.

BEST MODE OF CARRYING OUT THE INVENTION

As the method for preparing an ester condensate of the present invention, there is no specific limitation as long as it is a method wherein esterification reaction is carried out by using a catalyst containing a zirconium(IV) compound and/or a hafnium(IV) compound and an iron(III) compound and/or a gallium(III) compound.

As for the esterification reaction of the method for preparing an ester condensate of the present invention, reactions such as a reaction of carboxylic acid and alcohol, a reaction of polycarboxylic acid and multiple alcohol, and so on can be exemplified. As for the carboxylic acid used in the esterification reaction, any one of monocarboxylic acid of the group comprising chain or cyclic fatty acids or aromatic acids and monocarboxylic acids having unsaturated bond or substituents thereto can be used. Followings are included in the examples; acetic acid; propionic acid; n-butyric acid; isobutyric acid; n-valeric acid; isovaleric acid; methylethyl acetic acid; trimethylacetic acid; fatty acids such as caproic acid, enanthic acid, caprylic acid, pelargonic acid, capric acid, undercylic acid, lauric acid, tridecylic acid, myristic acid, pentadecylic acid, palmitic acid, heptadecylic acid, stearic acid, acylic acid, crotonic acid, isocrotonic acid, undercylenic acid, oleic acid, elaidic acid, erucic acid, brassidic acid, sorbic acid, linoleic acid and linolenic acid; and aromatic acids such as benzoic acid. As for the polycarboxylic acid, followings are included in the examples: dicarboxylic acids such as malonic acid, succinic acid, glutaric acid, adipic acid, pimelic acid, suberic acid, azelaic acid, sebacic acid, dodecanedioic acid, fumaric acid, maleic acid, mesaconic acid, citraconic acid, phthalic acid, terephtalic acid, isophtalic acid, and diphenyl ether-4,4'-dicarboxylic acid; tricarboxylic acids such as butane-1,2,4-tricarboxylic acid, cyclohexane-1,2,3-tricarboxylic acid, benzene-1,2,4-tricarboxylic acid, and naphthalene-1,2,4-tricarboxylic acid; tetracarboxylic acids such as butane-1,2,3,4-tetracarboxylic acid, cyclobutane-1,2,3,4-tetracarboxylic acid, benzene-1,2,4,5-tetracarboxylic acid, 3,3',4,4'-benzophenone tetracarboxylic acid, and 3,3',4,4'-diphenylether tetracarboxylic acid.

The alcohol used for the esterification in the present invention, may be primary, secondary, or tertiary alcohol, or it may be any alcohol such as one having a substituent of linear or cyclic alkyl group, alkenyl group, or aryl group. As to the alcohols, followings are included in the examples of monohydric alcohols: aliphatic primary alcohols such as methanol, ethanol, n-propanol, n-butanol, n-hexanol, n-heptanol, n-octanol, n-decanol, n-dodecanol, stearyl alcohol, 2-ethylhexan-1-ol and neopentyl alcohol; aromatic primary alcohols such as benzyl alcohol; aliphatic secondary alcohols such as isopropyl alcohol, s-butyl alcohol, 1-methylhexan-1-ol; alicyclic secondary alcohols such as cyclohexanol and 2-adamanthirol; tertiary alcohols such as t-butyl alcohol, 1-adamanthirol, phenol, o-cresol, m-cresol, p-cresol, 3,5-dimethylphenol, .alpha.-naphtol and .beta.-naphtol. Further, as to multiple alcohols, followings are included in the examples: ethylene glycol, propylene glycol, trimethylene glycol, 1,4-butanediol, 1,5-pentanediol, 1,6-hexanediol, 1,7-heptanediol, 1,8-octanediol, pinacol, neopentyl glycol, trimethylol propane, trimethylol ethane, pentaerythritol, dipentaerythritol, sorbitol, and polyvinyl alcohol. One or more of these alcohols can be suitably selected. Ester condensate can be produced chemoselectively, for instance, condensation reaction with bulky carboxylic acid and a primary hydroxyl group is caused selectively with the multiple alcohols having a primary hydroxyl group and a secondary hydroxyl group. Moreover, the further the distance between the primary hydroxyl group and the secondary hydroxyl group extends, the more selectively the condensation reaction with the primary hydroxyl group can be caused.

In the esterification reaction of the method for preparing an ester condensate of the present invention, equimolar amounts of carboxylic acid and alcohol may be used. When a monovalent carboxylic acid and a monohydric alcohol are used respectively as the carboxylic acid and the alcohol, an ester monomer is obtained, and when a polycarboxylic acid such as .alpha., .omega.-aliphatic dicarboxylic acid and a multiple alcohol such as .alpha., .omega.-aliphatic diol are used, a polyester can be synthesized. Furthermore, polyester can be synthesized also when .omega.-hydroxycarboxylic acid containing a hydroxyl group at one of the terminals and a carboxy group at another terminal respectively in a molecule, is used as the carboxylic acid and the alcohol. Followings are included in the examples of the .omega.-hydroxycarboxylic acid: .omega.-hydroxyundecanoic acid, hydroxydodecane acid, p-hydroxybenzoic acid, m-hydroxybenzoic acid, 6-hydroxynaphthalene-2-carboxylic acid, 4-.omega.-hydroxyphenoxy)benzoic acid, 3-.omega.-hydroxyphenoxy)benzoic acid, 4-(m-hydroxyphenoxy)benzoic acid, and 3-(m-hydroxyphenoxy)benzoic acid.

As for the zirconium(IV) compound contained in the catalyst used in the method for preparing an ester condensate of the present invention, any zirconium(IV) compound will suffice as long as it is a compound having tetravalent zirconium in the molecule, for instance, it may be a compound represented by a general formula (3):

$$ZrX_4Y_e \quad (3),$$

wherein X represents a halogen atom, Y represents tetrahydrofuran, and e represents 0 or 2. Specifically, halides such as zirconium fluoride ($ZrF_4$), zirconium chloride ($ZrCl_4$), zirconium bromide ($ZrBr_4$), and zirconium iodide ($ZrI_4$); and ether complexes wherein tetrahydrofuran is coordinated to these zirconium(IV) halides, in particular, $ZrF_4.(THF)_2$, $ZrCl_4.(THF)_2$, $ZrBr_4.(THF)_2$, $ZrI_4.(THF)_2$, and the like, can be listed. Moreover, besides the above tetrahydrofurans, it may be ether complexes or amid complexes having high stability to water, wherein ether ligands or amide ligands are coordinated to zirconium(IV) halides and the like. As for the amide ligands, followings are included in the examples: the amide compounds such as N,N-dimethylformamide, N,N-dimethylacetamide, N,N-diacetamide, and N-aceto-2-ketooxazolidine, which are represented by the structural formula: $R^3CONR^4R^5$, wherein $R^3$ represents a hydrogen atom, an alkyl group, an acyl group or an alkoxyl group, and $R^4$ and $R^5$ represent hydrogen atoms, alkyl groups, acyl groups, and alkoxy carbonic groups independently, and $R^3$ to $R^5$ may be bond together to form a circle. Other than above, as for the zirconium(IV) compounds used in the method for preparing an ester condensate of the present invention, sulfates such as zirconium sulfate ($Zr(SO)_4$), and alkyl zirconium(IV) compounds such as dicyclopentadienyl zirconium(IV) dichloride, can be exemplified. Further, a zirconium oxide dihalide hydrate represented by the structural formula: $Zr(IV)X_2O.nH_2O$ can be exemplified as a zirconium(IV) compound catalysts, which can be repeatedly used. The zirconium oxide dihalide hydrate is obtained as follows: esterification reaction is carried out by using zirconium(IV) halide salts and the like as a catalyst, and after the reaction is finished, the catalyst is extracted with hydrochloric acid aqueous solution, and condensation operation is stopped when a solid is deposited in the process of condensation of the extract of the hydrochloric acid aqueous solution. In the above structural formula, X represents a halogen atom and n represents an integer, wherein n is 6 or more, preferably n is 8. As the zirconium oxide dihalide hydrate, zirconium oxide difluoride hydrate, zirconium oxide dichloride hydrate, zirconium oxide dibromide hydrate, zirconium oxide diiodide hydrate, and the like can be exemplified.

Further, as the zirconium(IV) compound contained in the catalyst used in the method for preparing an ester condensate of the present invention, a compound represented by a general formula (1):

$$Zr(OH)_a(OR^1)_b \quad (1),$$

wherein, $R^1$ represents an acyl group or an alkyl group, and each of a and b is 0 or any one of integers of 1 to 4 and the relationship of a+b=4 is satisfied), can be exemplified. In the general formula (1), as the acyl group represented by $R^1$, acetyl group, propionyl group, butyryl group, isobutyryl group, valeryl group, isovaleryl group, hexanoyl group, benzoyl group and the like can be specifically exemplified. As the zirconium(IV) compound represented by the general formula (1), followings are included in the specific examples: zirconium(IV) tetraacetate, zirconium(IV) triacetatehydroxide, zirconium(IV) diacetate dihydroxide, zirconium(IV) acetate trihydroxide, zirconium(IV) tetrahydroxide, zirconium(IV) tetrapropionate, zirconium(IV) tripropionate hydroxide, zirconium(IV) dipropionate dihydroxide, zirconium(IV) propionate trihydroxide, zirconium(IV) tetraisopropionate, zirconium(IV) triisopropionate hydroxide, zirconium(IV) diisopropionate dihydroxide, zirconium(IV) propionate trihydroxide, zirconium(IV) tetrabutyrate, zirconium(IV) tributyrate hydroxide, zirconium(IV) dibutyrate dihydroxide, and zirconium(IV) butyrate trihydroxide.

Further, as the alkyl group represented by $R^1$ in the general formula (1), methyl group, ethyl group, propyl group, isopropyl group, butyl group and the like can be exemplified. As the zirconium(IV) compound represented by the general formula (1) having the $R^1$, zirconium(IV) alkoxide such as zirconium (IV) methoxide, zirconium(IV) ethoxide, zirconium(IV) propoxide, zirconium(IV) isopropoxide, zirconium(IV) butoxide, zirconium(IV) isobutoxide, zirconium(IV) t-butoxide, and zirconium(IV) pentyloxide, can be specifically exemplified.

As for the hafnium (IV) compound contained in the catalyst used in the method for preparing an ester condensate of the present invention, it may be any compound as long as it has tetravalent hafnium in the molecule, for instance, it may be a compound represented by a general formula (4):

$$HfX_4Y_f \quad (4),$$

wherein X represents a halogen atom, Y represents tetrahydrofuran, and f represents 0 or 2. Specifically, followings can be exemplified: halides such as hafnium fluoride ($HfF_4$), hafnium chloride ($HfCl_4$), hafnium bromide ($HfBr_4$), and hafnium iodide ($HfI_4$); and ether complexes wherein tetrahydrofurans are coordinated to these hafnium(IV) halides. Specifically, $HfF_4.(THF)_2$, $HfCl_4.(THF)_2$, $HfBr_4.(THF)_2$, $HfI_4.(THF)_2$, and the like can be exemplified. Moreover, besides the above tetrahydrofurans, it may be an ether complex or an amid complex having high stability to water, wherein ether ligands or amide ligands are coordinated to hafnium(IV) halides. As for the amide ligands and the ether ligands, the same ligands as those of the zirconium (IV) compound stated above, can be listed. Other than above, as for the hafnium(IV) compounds used in the method for preparing an ester condensate of the present invention, sulfates such as hafnium sulfate ($Hf(SO)_4$), and alkyl hafnium(IV) compounds such as dicyclopentadienyl hafnium(IV) dichloride, can be exemplified. Further, a hafnium oxide dihalide hydrate represented by the structural formula: $HfX_2O.nH_2O$, can be exemplified as a hafnium(IV) compound catalysts, which can be repeatedly used. The hafnium oxide dihalide hydrate is obtained as follows: esterification reaction is carried out by using a hafnium (IV) halide salts and the like as a catalyst, and after the reaction is finished, the catalyst is extracted with hydrochloric acid aqueous solution, and condensation operation is stopped when a solid is deposited in the process of condensation of the extract of the hydrochloric acid aqueous solution. In the above structural formula, X represents a halogen atom and n represents an integer, where n is 6 or more, preferably n is 8. As the hafnium oxide dihalide hydrate, hafnium oxide difluoride hydrate, hafnium oxide dichloride hydrate, hafnium oxide dibromide hydrate, hafnium oxide diiodie hydrate, and the like can be exemplified.

Further, as the hafnium(IV) compound contained in the catalyst used in the method for preparing an ester condensate of the present invention, the compound represented by a general formula (2):

$$Hf(OH)_c(OR^2)_d \quad (2),$$

wherein, $R^2$ represents an acyl group or an alkyl group, and each of c and d are 0 or any one of integers of 1 to 4 and the relationship of c+d=4 is satisfied can be exemplified. In the general formula (2), as the acyl group represented by $R^2$, acetyl group, propionyl group, butyryl group, isobutyryl group, valeryl group, isovaleryl group, hexanoyl group, benzoyl group and the like can be specifically exemplified. As the hafnium(IV) compound represented by the general formula (2), following can be exemplified: hafnium(IV) tetraacetate, hafnium(IV) triacetate hydroxide, hafnium(IV) diacetate dihydroxide, hafnium(IV) acetate trihydroxide, hafnium(IV) tetrahydroxide, hafnium(IV) tetrapropionate, hafnium(IV) tripropionate hydroxide, hafnium(IV) dipropionate dihydroxide, hafnium(IV) propionate trihydroxide, hafnium(IV) tetraisopropionate, hafnium(IV) triisopropionate hydroxide, hafnium(IV) diisopropionate dihydroxide, hafnium(IV) propionate trihydroxide, hafnium(IV) tetrabutyrate, hafnium (IV) tributyrate hydroxide, hafnium(IV) dibutyrate dihydroxide, and hafnium(IV) butyrate tri hydroxide.

Further, as the alkyl group represented by $R^2$ in the general formula (2), methyl group, ethyl group, propyl group, isopropyl group, butyl group and the like can be exemplified. As the hafnium(IV) compound represented by the general formula (2) having the $R^2$, hafnium(IV) alkoxide such as hafnium(IV) methoxide, hafnium(IV) ethoxide, hafnium(IV) propoxide, hafnium(IV) isopropoxide, hafnium(IV) butoxide, hafnium (IV) isobutoxide, hafnium(IV) t-butoxide, hafnium(IV) pentyloxide and the like, can be exemplified.

One or more of these zirconium(IV) compounds or hafnium(IV) compounds can be mixed for using as a catalyst, and its usage is not especially limited to. However, when ester is synthesized from carboxylic acid and alcohol, in the case where these compounds are used separately or in combination, 0.1 to 10 mol % or preferably 0.1 to 5 mol % as the total amount of the catalyst can be exemplified.

Iron(III) compounds and gallium(III) compounds used with the zirconium(IV) compounds/hafnium(IV) compounds contained in the catalyst used in the method for preparing an ester condensate of the present invention, are not especially limited to, but iron(III) alkoxide and gallium(III) alkoxide can be specifically exemplified. As for the alkoxide, followings can be exemplified: iron(II) methoxide, iron(II) ethoxide, iron(II) propoxide, iron(II) isopropoxide, iron(III) butoxide, iron(III) isobutoxide, iron(III) t-butoxide, iron(III) pentyloxide, gallium(III) methoxide, gallium(III) ethoxide, gallium(III) propoxide, gallium(III) isopropoxide, gallium (III) butoxide, gallium(III) isobutoxide and the like, gallium (III) t-butoxide, gallium(III) pentyloxide and the like. Among these, iron(III) methoxide, iron(III) ethoxide, iron(III) propoxide, iron(III) isopropoxide and the like can be listed as preferably specific examples, since they can prevent environmental destruction and they are available at low cost. One or more of these iron(III) compounds or gallium(III) compounds can be suitably selected and used in combination. These iron(III) compounds or gallium(III) compounds may be mixed into zirconium(IV) compounds and/or hafnium(IV) compounds prior to use as a composite metal salt catalyst, or they can be respectively added to the reaction system to use.

These iron(III) compounds and gallium(III) compounds can be used in the range of molar ratio of the above zirconium compound(IV) and/or hafnium(IV) compound to iron(III) compound and/or gallium(III) compound which is between 1 to 0.05 and 1 to 1, preferably between 1 to 0.1 and 1 to 1. Meanwhile, when two or more of them are used in combination, the above molar ratio is determined based on its total amount.

The solvent used in the method for preparing an ester condensate of the present invention, is not especially limited to, and it can be exemplified by a polar solvent, a mixed solvent of a polar solvent and a nonpolar solvent, and a nonpolar solvent. However, a nonpolar solvent is preferable in light of easiness of removing water outside of the reaction system, which is generated from esterification reaction. In other words, it is preferable to use a nonpolar solvent such as toluene to conduct heating reflux, and to easily remove azeotropic water from the reaction system. As to the method for removing the water, it can be exemplified by the method using known dehydrating agents such as calcium hydride or molecular sieves but the methods are not limited to these examples. Followings can be listed as the above-mentioned nonpolar solvents: toluene, xylene, mesitylene, pentamethylbenzene, m-terphenyl, benzene, ethylbenzene, 1,3,5-triisopropyl benzene, o-dichlorobenzene, 1,2,4-trichlorobenzene, naphthalene, and 1,2,3,4-tetrahydronaphthalene (tetralin). The followings are included in the examples of the polar solvent: ethers such as anisole, THF, 1,4-dioxane and the like: and others such as N-methyl-2-pyrrolidinone (N-methyl-2-pyrrolidone), N-butyl-2-pyrrolidinone (N-butyl-2-pyrrolidone), N-ethyl-2-pyrrolidone, 1,3,dimethyl-2-pyrrolidone, cresol, N,N-dimethylformamide, dimethyl acetamide, hexamethyl phosphoramide, dimethyl sulfoxide, diphenyl sulfone, nitrobenzene, benzonitrile, 1,3-dimethyl-2-imidazolidinone, gamma.-butyrolactone, phenol and the like. Moreover, when volatile alcohol such as methanol and the like is used as a substrate, the alcohol has an action also as a solvent, thus it is not necessary to use another solvent separately.

As for the esterification reaction in the method for preparing an ester condensate of the present invention, it is preferable to perform the reaction in a dried inactivate gas atmosphere, for example in an argon or a nitrogen atmosphere. The argon atmosphere can be formed, for example by the method for flowing argon, and by performing the reaction in the argon atmosphere, it is possible to achieve dehydration and deoxygenated atmosphere at the same time. For the condensation reaction of monovalent carboxylic acid with monohydric alcohol, and a polycondensation reaction of aliphatic polycarboxylic acid with aliphatic multiple alcohol, it is preferable to perform the reaction under heating reflux between 100° C. and 200° C., particularly between 120° C. and 160° C. for 1 to 24 hours. On the other hand, for a condensation reaction of aromatic carboxylic acid and aromatic alcohol, it is preferable to perform the reaction under heating reflux between 120° C. and 250° C., particularly between 150° C. and 200° C. for 24 to 72 hours. Since equimolar amount of carboxylic acid and alcohol are used, and no side reaction occurs, the purification of the monomeric ester or polyester obtained by these condensation reaction or polycondensation reaction can be carried out more simply than the conventional method by the known method.

After esterification reaction is finished, following are processed in order to reuse the used catalyst. Ionic liquids are added to the reaction system, the above composite salt catalyst of zirconium(IV) compound and/or hafnium(IV) compound and iron(III) compound and/or gallium(III) compound is extracted in an ionic liquid layer or a layer of hydrochloric acid solution by using the ionic liquid or the hydrochloric acid solution, and thereby the objective ester condensate is obtained from the organic layer. The ester condensate can be purified by the common method such as distillation or silica gel chromatography, as appropriate. Here, the ionic liquid is a salt having a property that it changes to liquid even at or around room temperature, whose polarity is high enough to melt metal salt well, so it can be preferably used in extraction of the catalyst used in the method for preparing an ester condensate of the present invention. The ionic liquid from which the catalyst is extracted can be used as the catalyst solution for the above esterification reaction as it is without condensation after being washed with diethylether as appropriate. The activity of the catalyst solution is remained after the esterification reaction even it is reused, so it is possible to reuse the catalyst solution. Hydrochloric acid solution can be exemplified as a solvent for using in extraction of the above composite salt catalyst, however, an ionic liquid is preferable in light of environmental protection. Any ionic liquid may be used for the ionic liquid for use in the method for preparing an ester condensate of the present invention, preferable liquids are exemplified by 1-butyl-3-methylimidazolium trifluoromethanesulfonimide, 1-ethyl-3-methylimidazolium trifluoromethanesulfonate, and N-alkylpyridinium trifluoromethane sulfonate imide, where N-butylpyridinium trifluoromethane sulfonate imide is particularly preferable. As for the usage of the ionic liquid, it is preferable when it is in the range between 0.5 and 2.0 ml to 0.05 mmol of the total usage of the above catalyst, more preferably, it is in the range between 1.0 and 1.5 ml.

Further, when the above catalyst solution is used in the method for preparing an ester condensate of the present invention, as for the solvent used in the ester condensation reaction, a low-polar organic solvent such as toluene or heptane is preferably used.

The present invention will be described in more detail by the following examples, while the technical scope of the present invention will not be limited to these examples.

Example 1

3 mol % of $Zr(OH)_x(OAc)_y$ (x+y=4) and 2 mol % of various metal salts were added into heptane solution of equimolar mixture of 4-phenylbutyric acid and cyclododecanol in a reaction container, and the mixture was heated to reflux for 6 hours, while the temperature of the oil bath was set to 120° C. The generated water was removed from the reaction system using a Dean-Stark fractionating apparatus. Then, the objective ester was obtained from the organic layer by extraction with diethyl ether. The ester was purified by distillation or using a silica gel column chromatography. The obtained ester conversion is shown in Table 1.

TABLE 1

| | Catalylst | Additive | Conversion (%) |
|---|---|---|---|
| 1 | $Zr(OH)_x(OAc)_y$ | — | 32 |
| 2 | $Ga(Oi-Pr)_3$ | — | 14 |
| 3 | $Fe(Oi-Pr)_3$ | — | 14 |
| 4 | $Ti(Oi-Pr)_4$ | — | 32 |
| 5 | $Zr(OH)_x(OAc)_y$ | $Zr(OH)_x(OAc)_y$ | 47 |
| 6 | $Zr(OH)_x(OAc)_y$ | $Ga(Oi-Pr)_3$ | 62 |
| 7 | $Zr(OH)_x(OAc)_y$ | $Fe(Oi-Pr)_3$ | 76 |
| 8 | $Zr(OH)_x(OAc)_y$ | $Ti(Oi-Pr)_4$ | 49 |

The result shows that catalytic activity was improved by adding gallium(III) isopropoxide ($Ga(Oi-Pr)_3$), iron(II) isopropoxide ($Fe(Oi-Pr)_3$) to $Zr(OH)_x(OAc)_y$.

Example 2

5 mmol of 2-tetrahydrofuroic acid, 5 mmol of benzyl alcohol, 0.5 mol % of zirconium(IV) isoproxide ($Zr(Oi-Pr)_4$), 2 mol % of iron(III) isopropoxide ($Fe(Oi-Pr)_3$), and 2.5 ml of octane were added into a reaction container, and the mixture was heated to reflux for 6 hours, while the temperature of the oil bath was set to 140° C. The generated water was removed from the reaction system using a Dean-Stark fractionating apparatus. After the reaction, resultant was once cooled to room temperature and 1 set of 1 M hydrochloric acid solution was added thereto, and the solution was stirred for 30 min at room temperature. Then, the objective ester was obtained from the organic layer by extraction with diethyl ether. The ester was purified by distillation or by using silica gel column chromatography. The yield was 99% or more.

Example 3

Figure 1:
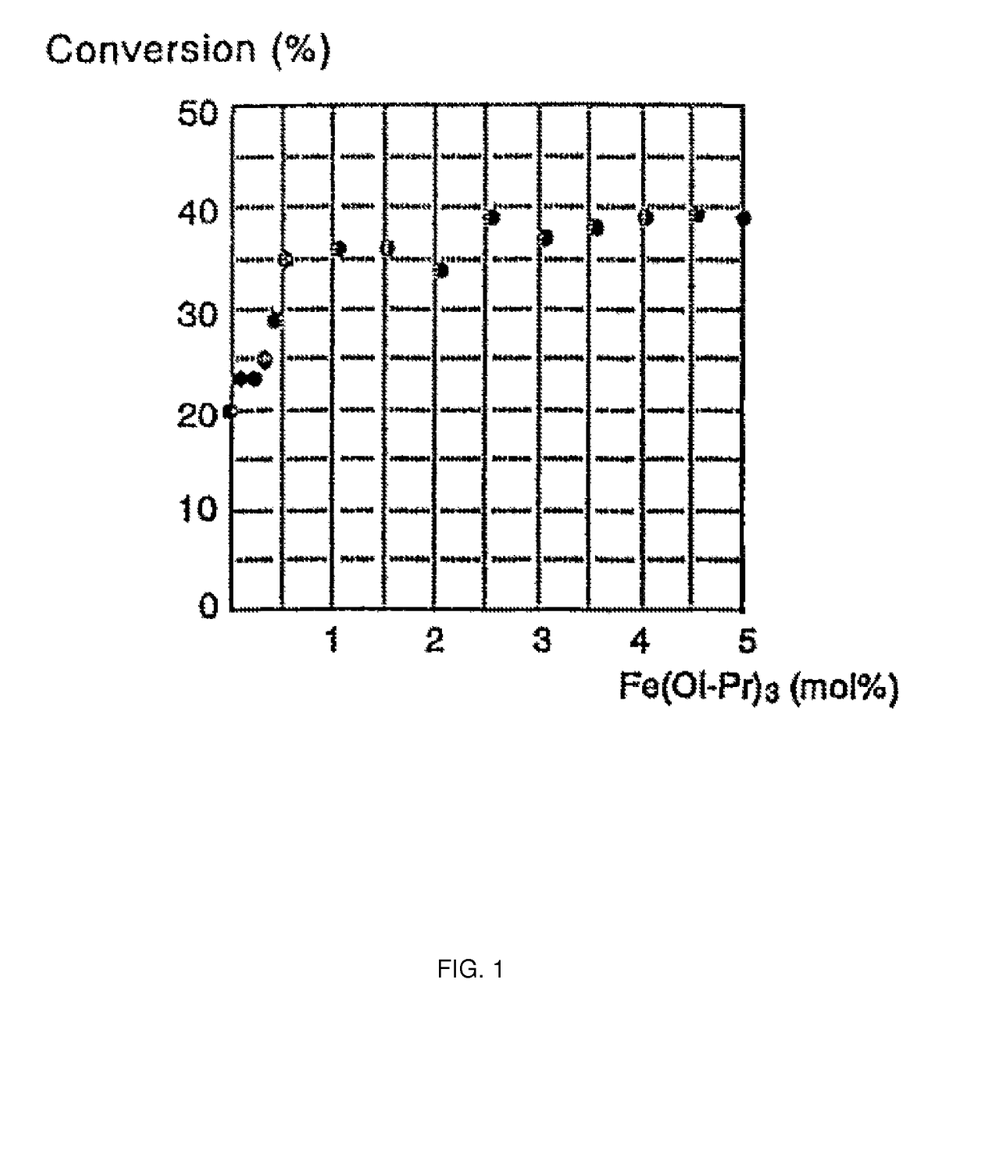
FIG. 1 represents the relationship between content rate of iron(III) isopropoxide to zirconium(IV) isoproxide and the ester conversion.

Reaction was performed with iron(III) isopropoxide($Fe(Oi-Pr)_3$) in the same manner as Example 1 but the adding amount to 10 mol % of zirconium(IV) isoproxide ($Zr(Oi-Pr)_4$) was changed and the temperature of the oil bath and the reaction time were set to 115° C. and 2 hours, respectively. The ester conversion is shown in Table 2 and FIG. 1.

TABLE 2

| Fe(Oi-Pr)$_3$ | Conversion (%) |
| --- | --- |
| 0 | 20 |
| 0.1 | 23 |
| 0.2 | 23 |
| 0.3 | 25 |
| 0.4 | 29 |
| 0.5 | 35 |
| 1.0 | 36 |
| 1.5 | 36 |
| 2.0 | 34 |
| 2.5 | 39 |
| 3.0 | 37 |
| 3.5 | 38 |
| 4.0 | 39 |
| 4.5 | 39 |
| 5.0 | 39 |

The result shows that 0.5 mol % or more of iron(III) isopropoxide (Fe(Oi-Pr)$_3$) to 10 mol % of zirconium(IV) isoproxide (Zr(Oi-Pr)$_4$) is required in order to optimize the adding effect of iron for the purpose of improving the catalytic activity.

Example 4

A composite metal salt catalyst comprising 3 mol % of zirconium(IV) isoproxide (Zr(Oi-Pr)$_4$), 3 mol % of hafnium (IV) isoproxide (Hf(Oi-Pr)$_4$), and 3 mol % of titanium(IV) isopropoxide(Ti(Oi-Pr)$_4$) were used for 4 mol % of iron(III) isopropoxide(Fe(Oi-Pr)$_3$), and a reaction was carried out in the same manner as Example 1 to investigate the change with time of the ester condensation reaction. The ester conversion is shown in Table 3.

TABLE 3

| Time (h) | Zr(Oi-Pr)$_4$ | Hf(Oi-Pr)$_4$ | Ti(Oi-Pr)$_4$ |
| --- | --- | --- | --- |
| 4 | 60 | 54 | 28 |
| 8 | 84 | 84 | 42 |
| 20 | 93 | 92 | 82 |

The result shows that Zr(IV)-Fe(III) and Hf(IV)-Fe(III) have approximately the same level of catalytic activity, and a significant accelerating effect on reaction is not seen with Ti(IV)-Fe(III).

Example 5

4 mol % of iron(III) isopropoxide (Fe(Oi-Pr)$_3$), 3 mol % of zirconium(IV) isoproxide (Zr(Oi-Pr)$_4$) were added to 4-phenylbutyric acid and 1,4-butanediol in hepetane solvent, while the mixture was heated to reflux at 115° C. for 5 hours. The yield of the obtained ester was 89%. When the reaction was carried out with 3 mol % of zirconium(IV) isopropoxide (Zr(Oi-Pr)$_4$) only, the yields of diester and monoester were 53% and 27%, respectively. The result shows that there was a clear difference in catalytic activity when iron(III) isopropoxide was used.

(Chemical formula 1)

After the reaction of Example 2, the aqueous layer from which zirconium(IV) and iron(III) were extracted, was used as it was to perform ester condensation reaction. The substrates shown in Table 4 and octane or toluene as a solvent were added to the aqueous layer containing zirconium(IV) and iron(III), and the mixture was heated to reflux at 120° C. or 140° C. for 6 hours to perform reaction. This operation was repeated. The yield of ester is shown in Table 4.

TABLE 4

$R^1CO_2H + R^2OH \xrightarrow[\text{dehydration reflux}]{140° C.}$ organic layer ⟶ $R^1CO_2R^2$ aqueos layer $\xrightarrow[\text{dehydration reflux}]{140 ° C.}$

| | $R^1CO_2H$ | $R^2OH$ | solvent hours | conversion (%) Run:1→2 →3→4 |
|---|---|---|---|---|
| 1 | (tetrahydrofuran-2-carboxylic acid) | $PhCH_2OH$ | octane 6 h | >99→>99→>99→>99 |
| 2 | $PhCO_2H$ | $PhOH_2OH$ | toluene 6 h | >99→>99 |

The result shows that even when the reaction was repeated by using the catalyst repeatedly, the catalytic activity was not reduced, and the catalyst can be recovered and reused.

Example 7

0.05 mmol of zirconium(IV) isoproxide (Zr(Oi-Pr)$_4$) and 0.05 mmol of iron(III) isopropoxide (Fe(Oi-Pr)$_3$) were added to the mixed solvent containing 2.5 ml of heptane and 0.25 ml of 1-butyl-3-methylimidazolium trifluoromethanesulfonimide as an ionic liquid. Next, 5 mmol of 4-phenyl-n-butyric acid and 5 mmol of benzyl alcohol were added thereto and the mixture was brought to azeotropic dehydration at 115° C. After 8 hours, the reaction solution was cooled to room temperature, hexane (8 ml)/ether (2 ml) were added thereto, the mixture was stirred for 30 min and left still for another 30 min, and the organic layer was separated therefrom. Extraction with hexane/ether was repeated until there was no starting material and product remaining in the ionic liquid layer (confirmed by TLC). The organic layers were collected and condensed, and ester was separated/purified by silica gel column chromatography and isolated 98% or more in yield. On the other hand, the remained ionic liquid layer per se was used for the following reaction. To this ionic liquid containing metal species, 2.5 ml of heptane, 5 mmol of 4-phenyl-n-butyric acid, 5 mmol of benzyl alcohol were added, and the mixture was brought to azeotropic dehydration at 115° C. for 8 hours. After the reaction solution was cooled to room temperature, the ionic liquid layer was washed in the same manner as described above to repeat the reuse. Recovery/reuse of the ionic liquid containing metal species was attempted 5 times or more, and 98% or more of chemical yield of ester was obtained in every attempt.

Example 8

To 2.5 ml of heptane solution containing 5 mmol of 4-phenylbutyric acid and 5 mmol of benzyl alcohol, and containing zirconium(IV) isoproxide (Zr(Oi-Pr)$_4$) and/or iron(III) isopropoxide (Fe(Oi-Pr)$_3$), ionic liquid (1-butyl-3-methylimidazolium trifluoromethanesulfonimide ([BMIM][NTf.sub.2]) or N-butylpyridinium trifluoromethane sulfonate imide ([BPY] [NTf.sub.2]) in predetermined amount was added, and the mixture was brought to azeortopic dehydration (bath temperature: 115° C.) for 8 hours by heating to reflux. After the reaction was finished, hexane (2 ml) was added thereto in order to separate the hydrocarbon layer from the ionic liquid layer. The amounts of zirconium(IV) and iron(III) in the ionic liquid layer were calculated by ICP (inductive coupled plasma) emission spectroscopic analysis. The result is shown in Table 5.

TABLE 5

| | Catalyst (mmol) | | | Recovery Rate (%) | |
|---|---|---|---|---|---|
| Test | Zr(IV) | Fe(III) | Ionic Liquid (ml) | Zr(IV) | Fe(III) |
| 1 | 0.05 | — | [BMIM] [NTf$_2$]: 1 | 4 | — |
| 2 | 0.05 | 0.05 | [BMIM] [NTf$_2$]: 1 | 75 | 78 |
| 3 | 0.025 | 0.025 | [BMIM] [NTf$_2$]: 3 | 92 | >99 |
| 4 | 0.05 | 0.05 | [BPY] [NTf$_2$]: 1 | >91 | >99 |

The result shows that 1-butyl-3-methylimidazolium trifluoromethanesulfonimide is useful for recovering catalysts (test 2), because iron(III) and zirconium(IV) were found that they efficiently moved to the ionic liquid layer, when iron(III) isopropoxide in a quantity equal to zirconium(IV) isopropoxide was added, while when zirconium(IV) isoproxide was used as a single catalyst, zirconium(IV) was left in the heptane layer (test 1). As for quantity, 3 ml of ionic liquid was necessary to extract zirconium(IV) (0.025 mmol) and iron(III) (0.025 mmol) (test 3). Further, it was also demonstrated that: zirconium(IV) and iron(III) can be extracted almost completely, by using N-butylpyridinium trifluoromethanesulfonimide, and N-butylpyridinium trifluoromethanesulfonimide is more useful than 1-butyl-3-methylimidazolium trifluoromethanesulfonimide (test 4).

Example 9

To 2.5 ml of the solution containing 5 mmol of carboxylic acid and 5 mmol alcohol, and containing 1 mol % of zirconium(IV) isoproxide (Zr(Oi-Pr)$_4$) and 1 mol % of metallic isoproxide (M(Oi-Pr)$_3$), 1 ml of N-butylpyridinium trifluoromethane sulfonate imide (ionic liquid) was added, and the mixture was brought to azeortopic dehydration by heating to reflux (bath temperature: 115° C.) for predetermined length of time. The reaction solution was cooled to room temperature, hexan (8 ml)/ether (2 ml) was added thereto, the solution was stirred for 30 min and left still for another 30 min, and the organic layer was separated therefrom. Extraction with hexane/ether was repeated until there was no starting material and product remaining in the ionic liquid layer (confirmed by TLC). On the other hand, the remained ionic liquid layer per se was used for the following reaction. Meanwhile, in test 4, 100 mmol of carboxylic acid and 100 mmol of alcohol were used, 0.1 mol % of zirconium(IV) isoproxide (Zr(Oi-Pr)$_4$) and 0.1 mol % of iron(III) isopropoxide (Fe(Oi-Pr)$_3$) were used, 10 ml of the solvent was used, and 2 ml of N-butylpyridinium trifluoromethane sulfonate imide as used. The result is shown in Table 6.

TABLE 6

| Test | Carboxylic Acid + Alcohol | Metallic Isopropoxide (M(Oi-Pr)₃) | Solvent Reaction Time (h) | Ester Yield with Last Extraction (%) [Number of Attempts to Reuse the Catalyst] |
|---|---|---|---|---|
| 1 | 4-phenylbutyric acid + benzyl alcohol | Fe(III) | heptane: 8 | 99 (15) |
| 2 | 4-phenylbutyric acid + benzyl alcohol | Ga(III) | heptane: 8 | 98 (3) |
| 3 | 4-phenylbutyric acid + benzyl alcohol | Fe(III) | octane: 12 | 99 (2) |
| 4 | 4-phenylbutyric acid + cyclododecanol | Fe(III) | octane: 12 | >99 (3) |
| 5 | PhCo₂H + benzyl alcohol | Fe(III) | toluene: 7 | 97 (3) |

The zirconium(IV)-iron(III) catalyst could be recycled repeatedly as a solution of N-butylpyridinium trifluoromethane sulfonate imide without being isolated (tests 1 and 3 to 5). For example, in test 1, zirconium(IV)-iron(III) catalyst (1 mol %) could be reused 15 times or more in esterification reaction of 4-phenylbutyric acid and benzyl alcohol in a biphasic solvent consisting of hepetane and N-butylpyridinium trifluoromethane sulfonate imide, without losing its activity at all. Likewise, ium(IV)-gallium(III) catalyst could also be reused as a on of N-butylpyridinium trifluoromethane sulfonate imide (test 2).

INDUSTRIAL APPLICABILITY

The method for preparing an ester condensate of the present invention, can significantly improve the catalytic activity beyond expectation, in esterification reaction of equimolar amounts of carboxylic acid and alcohol, by bringing an iron(III) compound and/or a gallium(III) compound to existence in a zirconium(IV) compound and/or a hafnium (IV) compound catalysts, and it can prevent generation of by-products, and it can prepare an ester condensate efficiently. The catalyst, exhibiting an excellent catalytic efficiency, can be used repeatedly without reducing the catalytic efficiency; it is thus reusable. Accordingly the method of the present invention is preferable in view of green chemistry. Since it allows to prepare an ester condensate in large quantity at low cost, it is also preferable as a method for industrially preparing an ester condensate which is resulted from the most basic organic reaction. The present invention is thus highly valuable in organic synthesis.

The invention claimed is:

1. A method for preparing an ester condensate, comprising performing an esterification reaction of carboxylic acid and alcohol using a catalyst containing a zirconium (IV) compound and either an iron(III) compound or a gallium(III) compound, wherein the zirconium (IV) compound is a compound represented by a general formula (1):

$$Zr(OH)_a(OR^1)_b \tag{1}$$

where $R^1$ is an acyl group or an alkyl group; and a and b each independently represents 0 or any one of integers of 1 to 4 with the relationship of a+b=4 is satisfied.

2. A method for preparing an ester condensate, comprising performing an esterification reaction of carboxylic acid and alcohol using a catalyst containing a zirconium (IV) compound and either an iron(III) compound or a gallium(III) compound, wherein the zirconium (IV) compound is a compound represented by a general formula (3):

$$ZrX_4Y_e \tag{3}$$

where X represents a halogen atom; Y represents tetrahydrofuran; and e represents 0 or 2.

3. A method for preparing an ester condensate, comprising performing an esterification reaction of carboxylic acid and alcohol using a catalyst containing a hafnium(IV) compound and either an iron(III) compound or a gallium(III) compound wherein the hafnium (IV) compound is a compound represented by a general formula (2):

$$Hf(OH)_c(OR^2)_d \tag{2}$$

where R2 represents an acyl group or an alkyl group; and c and d each independently represents 0 or any one of integers 1 to 4 with the relationship of c+d=4 is satisfied.

4. A method for preparing an ester condensate, comprising performing an esterification reaction of carboxylic acid and alcohol using a catalyst containing a hafnium(IV) compound and either an iron(III) compound or a gallium(III) compound wherein the hafnium (IV) compound is a compound represented by a general formula (4):

$$HfX_4Y_f \tag{4}$$

where X represents a halogen atom; Y represents tetrahydrofuran; and f represents 0 or 2.

5. The method for preparing an ester condensate according to any one of claims 1 to 4, wherein the iron compound is iron(III) alkoxide, and the gallium compound is gallium(III) alkoxide.

6. The method for preparing an ester condensate according to any one of claims 1 to 4, wherein the abundance of the iron compound is 5 mol % or more in relation to the zirconium (IV) compound or the hafnium (IV) compound.

7. The method for preparing an ester condensate according to any one of claims 1 to 4, wherein the esterification reaction is carried out by heating to reflux with a solvent, and removing azeotropic water from a reaction system.

8. The method for preparing an ester condensate according to claim 7, wherein a nonpolar or a low-polar solvent is used as the solvent.

9. The method for preparing an ester condensate according to claim 8, wherein the nonpolar or the low-polar solvent is one or more of solvents selected from the group of toluene, xylene, mesitylene and anisole.

10. The method for preparing an ester condensate according to any one of claims 1 to 4, wherein an ionic liquid is added to the reaction system after the esterification reaction is finished, ester is obtained from an organic layer, and then an ionic liquid layer per se is used as a catalytic solution.

11. The method for preparing an ester condensate according to claim 10, wherein the ionic liquid is 1-butyl-3-methyl imidazolium trifluoromethanesulfonimide, 1-ethyl-3-methylimidazolium trifluoromethanesulfonate.

12. The method for preparing an ester condensate according to any one of claims 1 to 4, wherein a hydrochloric acid aqueous solution is added to the reaction system after the esterification reaction is finished, ester is obtained from an organic layer, and then an aqueous layer per se is used as a catalytic solution.

13. The method for preparing an ester condensate according to claim 10, wherein the low-polar organic solvent selected from toluene and heptane is used as the solvent.

* * * * *

UNITED STATES PATENT AND TRADEMARK OFFICE
CERTIFICATE OF CORRECTION

| | | |
|---|---|---|
| PATENT NO. | : 7,973,193 B2 | |
| APPLICATION NO. | : 12/393519 | |
| DATED | : July 5, 2011 | |
| INVENTOR(S) | : Kazuaki Ishihara et al. | |

It is certified that error appears in the above-identified patent and that said Letters Patent is hereby corrected as shown below:

On the Title page, in Item (75), under "Inventors," in Column 1, Line 1, delete "Hisahi" and insert --Hisashi--.

Signed and Sealed this
Eighteenth Day of October, 2011

David J. Kappos
*Director of the United States Patent and Trademark Office*